United States Patent [19]

Ecanow et al.

[11] Patent Number: 4,874,742
[45] Date of Patent: * Oct. 17, 1989

[54] SYNTHETIC WHOLE BLOOD AND A PROCESS FOR PREPARING THE SAME

[75] Inventors: Charles S. Ecanow, Skokie; Bernard Ecanow, Wilmette, both of Ill.

[73] Assignee: Synthetic Blood Corporation, Deerfield, Ill.

[*] Notice: The portion of the term of this patent subsequent to Aug. 10, 1999 has been disclaimed.

[21] Appl. No.: 96,746

[22] Filed: Sep. 15, 1987

Related U.S. Application Data

[63] Continuation of Ser. No. 591,774, Mar. 21, 1984, abandoned, which is a continuation of Ser. No. 383,868, Jun. 1, 1982, Pat. No. 4,439,424, which is a continuation of Ser. No. 222,364, Jan. 5, 1981, Pat. No. 4,343,797, which is a continuation-in-part of Ser. No. 146,028, May 2, 1980, abandoned, which is a continuation-in-part of Ser. No. 47,071, Jun. 11, 1979, abandoned.

[51] Int. Cl.$^4$ .............................................. A61K 37/02
[52] U.S. Cl. ......................................... 514/2; 514/6; 424/94.1
[58] Field of Search ......................................... 514/2, 6

[56] References Cited

U.S. PATENT DOCUMENTS

| | | |
|---|---|---|
| 4,343,797 | 8/1982 | Ecanow et al. . |
| 4,439,424 | 3/1984 | Ecanow et al. . |
| 4,539,204 | 9/1985 | Ecanow et al. . |
| 4,547,490 | 10/1985 | Ecanow et al. . |
| 4,558,032 | 12/1985 | Ecanow et al. . |
| 4,596,788 | 6/1986 | Ecanow et al. . |

FOREIGN PATENT DOCUMENTS

| | | |
|---|---|---|
| 0083496 | 7/1983 | European Pat. Off. . |
| 0223906 | 3/1987 | European Pat. Off. . |
| 8302228 | 7/1983 | World Int. Prop. O. . |
| 8401717 | 5/1984 | World Int. Prop. O. . |
| 8505035 | 11/1985 | World Int. Prop. O. . |

*Primary Examiner*—Same Rosen
*Attorney, Agent, or Firm*—Mason, Kolehmainen, Rathburn & Wyss

[57] ABSTRACT

A composition and a method of making a whole blood substitute are disclosed. The claimed invention duplicates the two phase heterogeneous physico-chemical system of natural whole blood and accordingly, is capable of carrying out virtually all of the physiological functions of whole blood. Albumin dispersed in a solution composed of distilled water, sodium chloride and urea, and to which a surface active agent such as lecithin is subsequently added, constitutes the preferred method of preparing the two phase aqueous liquid system on which this invention is based. Other ingredients necessary to the manufacture of the claimed composition of matter include stroma free hemoglobin, an appropriate sterol, electrolytes and proteins. Emulsification of the two phase aqueous liquid system and the additives given immediately above completes the preparation of the claimed synthetic whole blood.

The method of manufacture described in this disclosure also provides for the separation of the phases of the two phase aqueous liquid system. Separation of the coacervate phase aqueous liquid system. Separation of the coacervate phase from the external equilibrium phase may be carried out prior to the introduction of the additives referred to above. In the preferred procedure, separation takes place after emulsification has been completed.

Introduction of the claimed synthetic whole blood into the circulation is accomplished through intravenous transfusion. When introduced into the circulation, the coacervate phase of this invention will serve the functions of normally occuring hematocrit.

19 Claims, No Drawings

SYNTHETIC WHOLE BLOOD AND A PROCESS FOR PREPARING THE SAME

This is a continuation of application Ser. No. 591,774, filed March 21, 1984, now abandoned, which is a continuation of application Ser. No. 383,868, filed June 1, 1982, now U.S. Pat. No. 4,439,424, which is a continuation of application Ser. No. 222,364 filed Jan. 5, 1981, now U.S. Pat. No. 4,343,797, issued Aug. 10, 1982, which is a continuation-in-part of application Ser. No. 146,029, filed May 2, 1980, abandoned, which is a continuation-in-part of application Ser. No. 47,071 filed June 11, 1979, abandoned.

BACKGROUND OF THE INVENTION

Authorities in the fields of physiology and clinical medicine have long recognized that an acceptable substitute for whole blood is needed. Recurrent shortages, adverse reactions, costs and the problems of storage are among the reasons which make a whole blood substitute a necessity. The need for a satisfactory substitute for hemaatocrit has been similarly recognized.

In the prior art, a number of compositions, ie: Lactated Ringer's Solution, Dextran, Modified Gelatin, Hydroethyl Starch, Fluorocarbons, Perfluorocarbons and Polyvinylprrolidones are referred to as "blood substitutes". *Reference: Chemical Abstracts, 8th Collective Index,* 1972 The scientific literature however, contains no evidence that any of these or any other known substance can function as a whole blood substitute or that they are conventionally used as such. The compositions referred to above are employed in one of two restricted ways: to expand plasma volume or to enhance oxygen transport Aside from their limited physiological function, the use of "blood substitutes" is highly restricted because of other shortcomings and the fact that some of the cited compositions have been associated with adverse reactions. Thus, an example of a common and serious shortcoming of available "blood substitutes" is the short period of time they are able to carry out the physiological function ascribed to them. Other reported difficulties associated with the compositions cited above follow:

Lactated Ringer's Solution

This solution provides electrolytes; to a limited extent, it will increase blood volume. However, it cannot safely sustain osmotic pressures nor can it transport and transfer oxygen, carbon dioxide or other physiological gases.

Dextran and Gelatin (including modified gelatin)

These substances can serve as plasma substitutes and expand circulatory volume. They cannot transport oxygen nor carry essential metabolites. It is known that Dextran can accumulate in tissues with adverse effect. The modified gelatins can alter in vivo coagulation phenomena and promote osmotic diuresis and other related changes. As is evident, such substances cannot be safely used when even slight kidney impairment is present. Further, fluid gelatins are known to be antigenic. Repeated administration of this composition can result in antibody production and lead to anaphylactic shock.

Albumin, Dextran and Hydroethyl Starch

These substances can expand plasma volume and increase oxygen transport but unlike the claimed composition, they cannot carry metabolites or essential amino acids. Dextran and Hydroethyl Starch have been reported to precipitate some of the clotting proteins from the plasma and thereby promote clot formation. Five percent albumin used for periods of from 2 to 3 hours has been known to produce pulmonary edema. Notably, albumin incorporated in the claimed Invention does not exert this effect.

Fluorocarbons

These entities cannot carry out the function of plasma. They can transport oxygen but they cannot dissolve nor transport essential electrolytes.

Perfluorochemicals

These entities must be prepared with a suitable plasma expander such as gelatin, etc. This requirement adds to the possibility of adverse reactions. Further, dwell times of perflurochemicals in tissues can be unacceptably long. In addition, since these substances must be emulsified, embolic reactions are likely unless very stable emulsions are achieved.

Polyvinylprrolidones

These compounds are no longer in use because of a demonstrated toxic accumulation in body tissues.

The prior art makes no reference to a blood substitute which has the physiological properties and the physicochemical structure of whole blood; that is, a substance capable of more than oxygen transport and or plasma volume expansion; nor does the art refer to a method of manufacture of such a composition. Further, the prior art contains no reference to a blood substitute which like whole blood possesses both polar and non polar properties. Presently known "substitutes" are principally either polar or non polar.

The scientific literature contains reports of the experimental and clinical use of a commercial perfluorochemical preparation known as Fluosol-DA. This composition is manufactured by the Green Cross Corporation, Osaka, Japan. It has been employed in perfusion experiments and recently, in treatment procedures designed to transport oxygen and increase plasma volume. Given its component ingredients and mode of manufacture, Fluosol-DA represents a product and an approach to the preparation of a blood substitute that is obviously different from that of the claimed invention which is based upon a coacervate equilibrium water system. A comparison of the components used in the manufacture of each follows:

| Composition of Fluosol-DA | Composition of Claimed Invention |
| --- | --- |
| Perfluorodecalin | Water |
| Perfluorotripropylamine | Albumin |
| Pluronic F-68 | Lecithin |
| Yolk phospholipids | NaCl |
| Glycerol | Kcl |
| NaCl | $CaCl_2$ |
| KCl | Cholesterol |
| $MgCl_2$ | Stroma Free Hemoglobin |
| $CaCl_2$ | |
| $NaHCO_3$ | Ingredients which can be |
| Glucose | added as needed: |
| Hydroethyl starch | Enzyme systems |
| | Metabolites |
| | Drug entities |
| | Nutrients |

The method of manufacture of Fluosol-DA is distinctly different from that used to prepare the claimed invention. Fluosol-DA cannot be prepared except as it uses an emulsifier and a plasma extender. Manufacture of the claimed composition does not use or require either substance. Once the emulsion of Fluosol-DA is prepared, it must be immediately frozen. This requirement makes it necessary to thaw the preparation prior to infusion. The claimed invention requires only refrigeration at from 4 to 10 degrees C. Thus the claimed composition can be used shortly after removal from refrigeration. Thawing is not involved and consequently, in contrast to Fluosol-DA there is little or no delay involved in infusing this invention.

Differences in the physiological properties between commonly used "blood substitutes" and the claimed invention are detailed in Table 1, page 6 of this disclosure.

blood substitute and those factors which make known substances, extenders of plasma, substitutes for erythrocytes etc. regardless of how they are presently classified.

Given the fact that none of the currently available "blood substitutes" possess the range of physiological function of whole blood, it is clear that what is needed in the art is a composition which can be safely used to replace whole blood. Several experts in the field have indicated the requirements for such a preparation, however no one has specified a composition which would meet the necessary requirements, nor has any method of manufacture been suggested in the literature.

TABLE 1

| Properties | Synthetic Whole Blood | Lactate Ringer's Solution | Dextran | Gelatin including modified gelatin | Albumin 5% | Hydroethyl Starch | Perfluoro- chemicals |
|---|---|---|---|---|---|---|---|
| 1. Oxygen Transport | Yes | No | No | No | No | No | Yes |
| 2. Carbon Dioxide Transfer | Yes | Yes | Yes | Yes | Yes | Yes | Yes |
| 3. Oxygen can be held in reserve and released in accordance with physiological tension | Yes | No | No | No | No | No | No |
| 4. Hemoglobin can be added or dispersed within the preparation without loss of stability | Yes | No | No | No | No | No | No |
| 5. Transfers gases other than $O_2$ and $CO_2$ | Yes | No | No | No | No | No | Yes |
| 6. Possesses both polar and non-polar properties | Yes | No | No | No | No | No | No |
| 7. Dissolves and transports non-polar drug entities without loss of dosage form stability | Yes | No | No | No | No | No | No |
| 8. Transports enzyme systems without loss of stability | Yes | No | No | No | No | No | No |
| 9. Effect on hematocrit percent after transfusion | Can be prepared to decrease or increase % | Reduction | Reduction | Reduction | Reduction | Reduction | Reduction |
| 10. Essential amino acids can be transported in stable form and desired quantity | Yes | Yes | Yes | Yes | Yes | Yes | Yes |
| 11. Oxygen uptake inhibited at low $O_2$ partial pressures | No | Does not apply | Does not apply | Does not apply | Does not apply | Does not apply | Yes |
| 12. Transports physiologically useful lipid soluble entities as a stable solution | Yes | No | No | No | No | No | Yes |

The preceeding table also establishes a number of additional facts which are relevant to this specification in that they relate to the practice of classifying a number of currently available substances, many with very limited physiological capability as "blood substitutes". This practice is misleading in that it fosters the belief that these substances are substitutes for whole blood.

Aside from describing the requirements for an ideal blood substitute, the prior art specifies that the principal function of whole blood is the maintainance of the normal cellular environment. All component functions such as transport of oxygen, maintainance of oncotic pressures, etc. subserve the principal function of blood. It would follow then, that to qualify as a whole blood substitute, as opposed to a plasma substitute or an erythrocyte substitute, the substance must be capable of restoring and/or maintaining the normal cell environment.

The data of Table 1 demonstrates that with the exception of the claimed invention, none of the representative "blood substitutes" listed, can do more than restore or maintain important but nonetheless limited aspects of the normal cell environment. These facts are not presented to question the usefulness of the listed substances, but rather to draw attention to and emphasize those factors which make the claimed invention a whole Guyton, and Best and Taylor have stated that an ideal whole blood substitute must be non toxic; isotonic with the contents of red blood cells; must not hinder normal plasma protein production; must have osmotic pressures and viscosity approaching that of whole blood, the particles of the substance must be of a size that the solution will not leave the circulation too freely; the substance should contain appropriate electrolytes to prevent derangement of the extracellular fluid electrolytes on administration. (*References; Guyton, Arthur, Basic Human Physiology, 2and Edition Saunders. Best, Charles and Taylor, Norman, The Physiological Basis for Medical Practice. 9th Edition, Williams and Wilkins.*

Geyer has emphasized the following additional features: the substance must be made from readily available synthetic (and/or endogenous) materials; the components of the composition must be known and can be varied to meet different needs; storage and shipping must present no serious problems; blood typing should be unnecessary, the substance should present no sensitivity problems; there should be no danger of hepatitis or transfusion transmitted disease; large volume usage should be possible and practical; addition of drugs, nutrients and other compounds should present no problems; gases in addition to oxygen and carbon dioxide should be able to be transported; the substance should spare natural blood supplies and finally, the blood substitute should not deteriorate in use. (*Reference: Jamieson, G. and Greenwalt, T. Eds. Proceedings 9th Annual Red Cross Symposium; Blood Substitutes and Blood Plasma* 1977, *Alan Liss, New York.*)

Tests of the claimed composition indicate that, it meets each of the seventeen requirements listed above. No other known manufactured substance is capable of doing so.

The Physicochemical Structure of Whole Blood

It is evident from a physicochemical point of view that in the body, blood exists and functions as a coacervate equilibrium water system; ie; as a two phase heterogeneous equilibrium system. The erythrocytes are largely composed of water and comprise the relatively non polar coacervate phase. The plasma of whole blood which also consists primarily of water constitute the bulk water, relatively polar aqueous phase of the two phase system. As is apparent from the polarities the physicochemical state of the water differs in each of the two phases. However, they are in equilibrium with respect to dissolved molecules and electrolytes. Any change that will significantly affect the components or their concentration will disturb the steady state with consequent physiological effect. Thus, as one example, alteration of the electrolyte content of the plasma (ie. change in the relatively polar water state) can result in destruction of the erythrocytes (ie: change in the non polar coacervate phase) with consequent hemolysis.

In this invention the method of manufacture results in a substance that successfully duplicates the two phase physicochemical system of whole human blood. This duplication enables the claimed composition to carry out virtually all of the physiological functions of whole human blood.

OBJECTS

It is an object of this invention to provide an acceptable substitute for whole blood. It is another object to provide a convenient method for preparing an acceptable substitute for whole blood. It is a further object to provide a substitute for the hematocrit and to provide a convenient method for preparing this substitute. Further objects will appear self evident from the disclosure.

THE INVENTION

This invention comprises a composition of matter useful as a substitute for whole natural blood and a method of manufacture thereof. The claimed invention makes use of a number of endogenous components and comprises a two phase aqueous liquid system identical to the physicochemical system of whole natural blood. A non polar coacervate phase insoluble in and in equilibrium with an associated polar liquid aqueous phase characterize both whole blood and the invented composition of matter.

This invention discloses a method of making a whole blood substitute which comprises the formation of a two phase aqueous liquid system. This two phase system is composed of an internal suspension phase, herein referred to as the coacervate phase and an external suspension phase which is the associated liquid aqueous phase. The internal phase comprises from 10 to 50% of the two phase system; the external phase makes up from 50 to 90% of the aqueous liquid system. The two phase system herein referred to, can be prepared by dispersing from 5 to 15% weight to volume of albumin in distilled water containing 0.9% weight to volume sodium chloride, 1 to 5% urea, and subsequently adding from 0.1 to 10.0% weight to volume of a surface active agent such as lecithin. Lecithin is the preferred surface active agent although any of the following phospholipids or mixtures thereof can be used in place of lecithin: cephalin, isolecithin, sphingomyelin, phosphatidyl serine, phosphatidic acid, phosphatidyl inositol and phosphatidyl choline. Other compounds known to those skilled in the art may also be used In this invention, an alternative method for preparing the two phase aqueous liquid system may be used in place of the procedure described immediately above. The alternative method combines a gelatin solution (IEP :8.2) and acacia USP with distilled water. The resulting solution is then adjusted, depending upon the desired effect, to a pH ranging in value from 7.5 to 9.5. Either sodium hydroxide or sodium bicarbonate can be used to adjust the pH value.

The methods of preparation described above are among the several which can be used. In the practice of this invention, the underlying principle is that any molecule or combination of molecules capable of forming a nontoxic two phase aqueous liquid system can be used in this step of the manufacturing process.

Irrespective of the method used, the mode of preparation used will always result in a two phase aqueous liquid system. This system as previously described will consist of a coacervate phase and an external equilibrium phase. It is important to emphasize that while the two phases will be composed of the same molecules, the concentration of the component molecules will be different in each of the two phases.

The coacervate or internal suspension phase possesses the physiological and physicochemical properties of hemato crit while the external aqueous phase is the physiological and physicochemical equivalent of blood plasma. The two phase aqueous liquid system is brought into even closer functional equivalence with whole blood when appropriate proteins, sterols, stroma free hemoglobin and electrolytes are added.

At the point that the manufacture of the two phase aqueous liquid system is completed, if it is desired, the two phases can be separated. In the preferred procedure, the two component phases are separated after the ingredients listed immediately above have been added to the system.

Upon separation of the phases, the coacervate phase can be safely intravenously introduced to institute or enhance the properties of hematocrit. Thus, it can transport and transfer oxygen and carbon dioxide much as naturally occuring erythrocyte without adversely affecting the percent of the recipient's hematocrit. The internal suspension phase, ie. coacervate phase, can carry nutrients, physiological entities, therapeutic drugs and metabolic agents, either in emulsified or nonemulsified form. The emulsified form is preferred. When the coacervate phase is introduced intravenously, it will disperse in the blood plasma of the recipient, and thereby contribute to the two phase physicochemical system of the naturally occuring whole blood. Further, the physicochemical characteristics of the internal suspension phase render it both sensitive to and reactive to physiological changes in the recipient's blood. Finally, this phase can readily enter and pass through the major blood vessels, capillaries and the microcirculation.

If the intended purpose is to transfuse the equivalent of whole blood, ( ie. plasma and hematocrit ) then the emulsified form of the two phase system will be introduced intravenously. In this form, this claimed composition can be safely used in a wide variety of treatment procedures including the establishment and maintainance of extra corporeal circulation. It readily circulates within the entire vascular system.

Upon transfusion the two phase equilibrium system of this invention can establish, reestablish and/or maintain normal osmotic pressures, transport and transfer physiological gases, can carry nutrients, drug dosage forms and various physiological entities in stable form over extended periods of time. The transport characteristics of these compositions of matter enable it to serve as a safe and reliable vehicle in hyperalimentation procedures. When it is desireable to introduce enzyme systems into the body, such systems can be added to the internal suspension phase of this invention and infused through conventional intravenous methods. Enzyme systems introduced through these compositions of matter will perform their normal physiological functions.

When the addition of stroma free hemoglobin to the two phase system is indicated, such addition does not effect the stability or the action of the additives referred to above.

The guidelines which determine the quantities of the claimed synthetic whole blood which may be safely infused are unlike those of "blood substitutes". They are identical to the guidelines which govern the use of whole blood.

Two additional unique features characterize the claimed composition, ie: it can be rendered free of foreign proteins and other elements that contribute to the adverse reactions associated with the transfusion of whole blood. Further, because this invention possesses universal donor characteristics no blood typing is necessary prior to administration of this composition.

By reason of its mode of manufacture and its physicochemical structure, the claimed whole blood substitute possesses a number of advantages over whole blood. Thus, prior to infusion this invention can be modified to meet many of the specific requirements of given treatment procedures, such as hyperalimentation, intravenous drug therapy, addition of metabolic enzymes, open heart surgery, etc. By way of example, additional quantities of stroma free hemoglobin can be incorporated in a given embodiment of this invention so as to enable more oxygen to be carried for longer periods of time as would be desirable in treatment of certain blood diseases or in instances of prolonged surgery. Electrolytes can be added to the claimed substance for use in the treatment of cases of severe burns or shock resulting from the loss of blood. In embodiments containing added electrolytes, adjustments to isotonicity are made following such additions. When nutrients must be quickly introduced and/or when the circulatory system is the preferred route for nutrition, essential amino acids and other nutritional agents can be added to the coacervate phase of the embodiment prior to emulsification and transfusion into the recipient.

Other important advantages of this invention may be enumerated as follows: the components of the claimed composition are abundant, readily available and inexpensive. They can be prepared from natural substances or from non toxic synthetic sources. Additives can be quickly introduced to previously prepared, stored embodiments. The invention can be used without the need for highly specialized equipment or technology. The constituents of the claimed composition of matter and the method of preparing it eliminates the problems associated with the storage of whole blood.

Additionally, this invention comprises a method of making the compositions listed above. The preferred method comprises consists of forming the two phase aqueous liquid system by dispersing powdered albumin in distilled water which contains 0.9% weight to volume sodium chloride, i to 5% weight to volume urea. A surface active agent is added to this solution at the appropriate point in the manufacturing process. Lecithin is the preferred surface active component. In this method, the amount of albumin used can range from 5 to 15 percent weight to volume of the coacervate phase of the two phase system. The quantity of lecithin that is added can range from 0.1 to 10.0 percent weight to volume of the concervate phase. In using these ingredients an essential requirement that must be observed is that in selecting any given ratio of albumin to lecithin, the concentration of albumin must always be greater than that of lecithin in order to achieve the optimal two phase heterogeneous system. Additionally, this invention comprises a method of making a substitute for the coacervate phase of whole blood.

In the practice of this invention, the two phase aqueous system is brought into closer approximation with whole blood by adding appropriate amounts of the following ingredients: urea, electrolytes, stroma free hemoglobin and sterols. Certain treatment regimens may make the addition of mucopolysaccarides, glycoproteins, proteins and other molecules such as heparin desireable. These substances can be added to the claimed composition and will perform their conventional functions.

During the manufacture of this system, coacervated structured water insoluble aqueous droplets are formed. Under given conditions, these droplets can coalesce to form a coacervate layer. This layer can be readily emulsified in an isotonic solution to form droplets of any desired size. In this invention, the preferred size can range from two to nine microns. With the exception of distilled water and electrolytes, all other components may be selected from either synthetic or natural sources.

The prior art does not contain any reference to any composition of matter which can be safely substituted for and function physiologically virtually the same as natural whole blood. In no way does the prior art suggest or hint at a method of manufacture of synthetic whole blood which is based upon a two phase heterogeneous physicochemical system. Further, the prior art makes no reference to a substitute for hematocrit comprised of the coacervate phase of the two phase aqueous equilibrium system referred to immediately above.

DESCRIPTION

In order to more fully explain the invention, the following is a general example of the method of preparation of the invention and subsequent specific examples of the practice of this invention.

In the process of manufacture, the component ingredients are prepared and combined under aseptic conditions.

The first step in the manufacturing process consists of preparing a stock solution of 5 to 15% weight to volume of albumin. This is made by prewetting albumin powder with distilled water for twelve hours. The resulting solution is then refrigerated for twelve hours at a temperature that may range from 1 to 4 degrees C. At the end of this period, the solution is removed from refrigeration and additional distilled water containing 0.9% weight to volume of sodium chloride and 1 to 5% weight to volume of urea is added in an amount that will result in a 5% weight to volume albumin solution. Commercially available human albumin solutions, which are adjusted to isotonicity during their preparation may be used instead, thereby eliminating the foregoing steps. If powdered albumin is used in the manner described above, then adjustment to isotonicity is made at the appropriate point of the manufacturing process.

In order to complete the two phase aqueous liquid system, lecithin is introduced into the albumin solution referred to immediately above. The percent of lecithin that is added to the solution can range from 0.1 to 10.0 weight to volume. The solution that results from these procedures will contain 5% albumin and a given amount of lecithin, depending upon the amount added.

The next steps of formulation are as follows: the solution described above is thoroughly mixed by vortex mixer for ten minutes. It is then placed in a suitable glass container, sealed and stored undisturbed in a refrigerator at 10 degrees C for seven days. During this period of storage the solution will have separated into two distinct layers. The lower of these two layers comprises the internal suspension or coacervate phase of the two phase system. The upper layer constitutes the external suspension or equilibrium water Depending on the quantities of the materials which are used in the steps of manufacture, the coacervate phase of the now completed two phase system will comprise from 10% to 50% of the system. It must be emphasized that in preparing this invention the concentration of albumin must always be greater than that of lecithin to achieve the optimal system.

If it is desired, the coacervate phase may now be separated from its equilibrium aqueous phase by means of a separatory funnel. Upon separation the coacervate phase can be introduced into the circulation. It will then carry out the functions of hemtocrit. In the preferred practice of this invention, however separation of the two phases is not carried out until the preparation of the synthetic whole blood is completed.

An alternative method of preparing the two phase aqueous liquid system consists of the following procedure. Forty mls. of a 5% gelatin solution (IEP 8.2) is mixed with from 40 to 80 mls. of 12% acacia and distilled water. Sufficient distilled water is added until the final volume is 150 mls. The pH is adjusted to a point within the range of 7.5 to 9.5 using either sodium hydroxide or sodium bicarbonate. The resulting solution is left undisturbed for 24 hours at 10 degrees centigrade. At the end of this period the two phases will have separated from each other. If desired this preparation can then be used in place of the previously described coacervate system in the remaining steps of the manufacturing process. If immediate use is not intended, the preparation can be stored at 10 degrees C. until needed.

At this point of the manufacturing process, the two phase system is brought into closer chemical approximation to whole blood by adding 0.1% to 0.9% sodium chloride and 1% weight to volume of cholesterol. Other endogenous electrolytes such as calcium and potassium as the chloride salt are also added to the two phase system at this point, to the desired concentration. Small amounts of sodium bicarbonate are then added until the pH of the two phase system is in the range of 7.3 to 7.45. If necessary, the solution in the flask is made iso-osmtic with normal blood plasma by the further addition of such amounts of sodium chloride as are indicated and the addition of such quantities of distilled water as may be required. The flask containing the two phase system and the additives described above, is sealed, placed upon a shaker apparatus and agitated for one hour. It is then removed, placed in a refrigerator at 10 degrees C. and left undisturbed for seven days. At the end of this seven day period, the coacervate phase can be separated from its equilibrium aqueous phase using a separatory funnel. If desired, the remaining equilibrium liquid can be preserved for use to expand the two phase system at some later point. If the preparation of synthetic whole blood is intended, the entire two phase aqueous liquis system is emulsified using any of the recognized emulsification procedures to provide droplets of the desired size. In the practice of this invention, the preferred droplet size ranges from 2 to 9 microns. Five percent weight to volume of stroma free hemoglobin can be added, as desired, after emulsification has been completed.

Lecithin is a preferred ingredient in the preparation of this composition. However, any of the following phospholipids or mixtures thereof can be used in its place: cephalin, isolecithin, sphingomyelin, phosphatidyl serine, phosphatidic acid, phosphatidyl inositol, and phosphatidyl choline. Other compounds of this group known to those skilled in the art could also be used. Cholesterol is also used to prepare the synthetic whole blood which constitutes this invention. However, any of the following entities from the sterol group can also be used: ergosterol, 7- dehydrocholesterol, $\alpha$sitosterol, $\beta$sitosterol, $\gamma$sitosterol, campesterol and mixtures thereof. Other compounds of this group known to those skilled in the art may also be used.

If the intended use of these compositions of matter is to enhance and carry out the functions of hematocrit, the coacervate phase is infused into the body. If the purpose is to infuse the equivalent of whole blood, then the two phase equilibrium system is utilized.

In the event that enhanced oxygen and other physiological gas transport and transfer is desired, from 10% to 15% weight to volume stroma free hemoglobin is added to this system prior to infusion. If other physiological purposes are intended, ie: hyperalimentation, intravenous drug therapy, addition of metabolic enzymes, etc. the specific ingredients are added directly to the coacervate phase of the system prior to emulsification. The presence or absence of hemoglobin in this two phase system has no effect upon the action of these additives.

While the above description contains many specificities, these should not be construed as limitations on the scope of the invention but rather as exemplifications of preferred embodiments. Accordingly, the scope of this invention should not be determined by their described embodiments but by the appended claims and their legal equivalents.

SPECIFIC EXAMPLES

Examples of how the claimed compositions of matter may be prepared follow:

EXAMPLE 1

Sterile conditions are observed during all phases of manufacture. The step involving refrigeration takes place at 10 degrees C. All other processes are carried out at 25 degrees C. Twenty five grams of albumin is added to 500 mls. of distilled water containing 0.9% weight to volume sodium chloride, 3% weight to volume urea is also added. The resulting solution is then thoroughly mixed, placed in an appropriate glass container, sealed and left undisturbed in a refrigerator for twelve hours. 500 mls of a 2½% solution of lecithin is then added. The solution is placed in a 2 liter flat bottom flask and thoroughly mixed. The flask is again sealed and refrigerated for seven days. After this period, 1 gram of cholesterol and calcium and potassium as the chloride salt are then added in the amounts of 0.2 and 0.4 grams respectively. The solution is then adjusted to a pH ranging from 7.35 to 7.45 by introducing the necessary amounts of sodium bicarbonate. If necessary, the solution is made iso-osmotic with normal blood plasma by the further addition of such small amounts of sodium chloride and distilled water as are required. After adjustment to isotonicity, the flask is resealed and placed on a shaker apparatus. The solution is agitated for one hour and then stored, undisturbed in a refrigerator at a temperature of 10 degrees C for seven days. At the end of this period, the solution will have separated into two layers; the bottom one of which comprises the coacervate phase. The top layer constitutes the equilibrium water phase. The phases can be separated in the manner described previously, depending upon the intended end use of the composition. Alternatively, the two phase aqueous liquid system can be emulsified to give a suspension of globules or droplets which may range in size from 2 to 9 microns. The resulting emulsion can then be stored or introduced into the circulation intravenously.

EXAMPLE 2

Two hundred mls. of 2% lecithin solution is added to 200 mls of a 4% albumin solution in a two liter flat bottom flask. To this mixture, 9 grams of sodium chloride, 10 grams of urea and 1 gram of cholesterol are added. The remainder of the procedure follows Example 1.

EXAMPLE 3

200 mls of 4% isolecithin solution are added to 200 mls. of 5% albumin solution containing 0.9% weight to volume sodium chloride and 1% weight to volume urea in a 2 liter flat bottom flask. The rest of the procedure follows Example 1.

EXAMPLE 4

500 mls of 2½% lecithin solution are added to 500 mls. of 5% human albumin stock solution in a 2 liter flt bottom flask. To this mixture, 9 grams of sodium chloride, 9 grams of urea and 0.1 gram of ergosterol are added. The rest of the procedure follows Example 1.

EXAMPLE 5

500 mls of a 2½% solution of isolecithin are added to 500 mls of a 5% stock solution. To this mixture, 9 grams of sodium chloride, 9 grams of urea and 0.1 gram of ergosterol are added. The rest of the procedure follows Example 1.

EXAMPLE 6

This procedure follows Example 1 except that 50 grams of stroma free hemoglobin are added to the coacervate phase and thoroughly swirled in a flat bottom flask to achieve a uniform dispersion of the added hemoglobin.

EXAMPLE 7

The procedure follows Example 1 except that after the manufacture of the two phase system is completed, the coacervate phase is separated from its equilibrium aqueous phase by means of a separatory funnel. The separated coacervate phase can be introduced intravenously and will function as hematocrit.

EXAMPLE 8

40 mls. of a 5% weight to volume gelatin solution (iso-electric point: 8.2) is thoroughly mixed with 40 mls of 12% weight to volume acacia. Distilled water is added to this mixture until a volume of 150 mls. is reached. While gelatin solution with an iso-electric point of 8.2 is preferred, gelatin solutions with iso-electric points ranging from 4.0 to 9.0 may be used under given conditions. The pH of this example is adjusted within the range of 7.5 to 9.5 through the use of sodium hydroxide. The solution is the placed in a suitable glass container, sealed and left undisturbed in a refrigerator at 10 degrees C. for 24 hours. The two phase aqueous liquid system is completely formed at this point. If separation of the phases is desired, the coacervate phase can be separated from its equilibrium aqueous phase by means of a separatory funnel at this stage of the manufacturing process. If the end point use does not indicate separation, the two phase system prepared according to this example is emulsified by means of a colloid mill. 1% cholesterol, 5% stroma free hemoglobin are then added. In the preferred practice of this invention separation of the two phases is not carried out until the preparation of the synthetic whole blood is completed.

EXAMPLE 9

The procedure follows Example 1 except that after the two phase system is completed and emulsified essential amino acids such as L-lysine, L-tryptophan, L-histidine, L-phenylalanine, L-leucine, L-isoleucine, L-threonine, L-valine, L-orgnine, and L-methionine can be added in the amounts indicated by the needs of the individual situation.

EXPERIMENTS

The following are examples of in vivo administration of synthetic whole blood prepared in accordance with the detailed description.

EXPERIMENT 1

To each of three rats, a total of 8cc. of a freshly completed sample of the substitute whole blood of Example 1 was administered in two doses. The specific procedure involved the removal of 4 cc. of blood followed immediately by the infusion of 4 cc. of the synthetic whole blood. This procedure was repeated after an interval of five minutes. In effect, this experiment involved the removal and replacement of approximately 40% of the animal's total blood volume. One rat of this series was sacrificed two hours after the experiment was completed. Inspection of the lungs, heart and other tissues revealed no significant pathological changes. The remaining two animals were sacrificed sixty hours after the second infusion of the substitute whole blood. Examination of the heart, lungs and other tissues showed no pathological changes nor any signs associated with hypoxia, pulmonary edema or adverse immunological reaction. Blood studies of all animals in this series indicated normal oxygen and carbon dioxide tensions, and normal pH values. Neither the erythrocytes nor the clotting mechanisms appeared to be adversely affected.

EXPERIMENT 2

In a second experiment, one rat received a single injection of 6 cc. of a second preparation of the substitute whole blood of Example 1 immediately following removal of 6 cc. of its blood. This animal expired approximately 70 minutes after infusion of this sample of substitute blood. Tissue studies indicated signs of intravascular disseminated coagulation. Examination and analysis of this sample of the synthetic whole blood yielded evidence of contamination and improper preparation.

EXPERIMENT 3

Six cc. of a third preparation of the substitute whole blood of Example 1 was administered intravenously to each of two rats in a third series without withdrawal of blood from either animal. One rat was sacrificed after 48 hours; seventy two hours after infusion with substitute whole blood the second animal was sacrificed. Inspection of the tissues and red blood cells showed no pathological change or evidence of abnormal response. Clotting mechanisms appeared to be unaffected.

EXPERIMENT 4

A fourth series of tests was performed using two Nembutal anesthetized dogs. Approximately 10% of the first animal's blood was withdrawn from the femoral artery, and replaced immediately with an equal quantity of substitute whole blood of Example 1. Approximately 40% of the blood volume was withdrawn from the second dog and replaced with an equal quantity of the substitute whole blood of Example 3 Samples of the circulating blood were withdrawn from each animal from the site of infusion at three minute intervals for fifteen minutes and at one half hour intervals for two hours thereafter. Oxygen tension measurements were determined by the IL Blood Gas Analyzer. Test results indicated an increase in $PaO_2$ levels over base line measurements. Carbon dioxide levels remained within normal limits.

Mean arterial blood pressure rose to 150/88 from 135/80 after infusion in the first animal. The mean arterial blood pressure in the second animal rose from 130/75 to 155/90, following infusion with substitute whole blood. After 24 hours, the mean arterial blood pressure stabilized at 130/70 in the first dog, Mean arterial blood pressure in the second dog stabilized at 145/75 twenty four hours after infusion. Following infusion with synthetic whole blood, mean heart rate in the first animal rose to 120 beats per minute from a base line measurement of 105. Mean heart rate following infusion of the second dog rose to 155 beats per minute from a base line reading of 110. After 24 hours the mean heart rate was measured at 98. The mean heart of the second animal stabilized after 24 hours at 99 beats per minute. Both animals were sacrificed 96 hours after infusion with substitute whole blood. Tissue studies revealed no significant evidence of pathological change or abnormal immunological reaction in the first animal. The second dog however exhibited equivocal signs of intravacular disseminated coagulation in segments of the venous system. A third dog was exposed to the same withdrawal and replacement procedures as the second animal of this series. However, the infused substitute blood in this experiment contained 10 mls. of heparin. Sacrifice of this animal 96 hours after infusion and study of the organs, tissues and red blood cells revealed no abnormal changes or signs of immunologically undesireable response.

EXPERIMENT 5

In a fifth experiment utilizing one Nembutal anesthetized dog, the infused substitute whole blood of Example 1 was prepared to include stroma free hemoglobin. Approximately 40% of the blood volume of this animal was withdrawn and replaced with the preparation described immediately above. Mean blood pressure after infusion rose to 150/90 from a baseline measurement of 135/80; after 24 hours, the mean blood pressure stabilized at 140/85. Following infusion with substitute whole blood mean heart rate rose from 110 to 145 beats per minute. After 24 hours, the mean heart rate was measured at 105. $PaO_2$ levels remained increased over base line measurements for approximately 95 minutes. Upon restoration of base line $PaO_2$ levels, intermitant administration of oxygen from an external source resulted in elevated oxygen tensions in this animal that persisted for approximately six and one half hours. This result suggests that the claimed composition of matter remains in the circulation, retaining its ability to transport oxygen efficiently for an appreciable period of time.

EXPERIMENT 6

A sixth series of studies involved the withdrawal of 6 cc of blood from each of two rats and the immediate replacement with an equal amount of a substitute whole blood made in accordance with Example 8. Blood studies indicated elevated oxygen tensions, normal carbon dioxide levels and normal pH values. Both animals were sacrificed 72 hours after infusion of the synthetic whole blood. Inspection of the tissues revealed no significant evidence of pathological change or adverse immunological response.

CONCLUSION

In summary, a synthetic whole blood and a method of making this composition of matter are disclosed. The composition is comprised of a two phase aqueous liquid system with physiological properties that are very similar to those of natural whole blood. The claimed invention is prepared by dispersing albumin in a solution composed of distilled water, sodium chloride and urea and to which a surface active agent such as lecithin is subsequently added. The coacervate phase of this two phase system can be separated from its associated liquid phase. As such, it can be transfused and will function as an effective substitute for hematocrit. In manufacturing the whole blood substitute, other components such as electrolytes, stroma free hemoglobin and an appropriate sterol are added to the two phase aqueous liquid system which is then emulsified. This then results in a composition of matter whose physiological and physicochemical properties closely approximate those of natural whole blood. Experiments based on laboratory animals have demonstrated that this invention can be safely and effectively used as a substitute for natural whole blood, and further, that the coacervate phase of this two phase invention can be safely and effectively used as a substitute for hematocrit.

What is claimed is:

1. A synthetic whole blood substitute, comprising a non-toxic two phase liquid system, both said phases being aqueous, wherein;
   one of said phases is an aqueous liquid coacervate phase (internal suspension phase) which is relatively non-polar and which is capable, when introduced into a body's circulation, of functioning as a substitute for at least part of the erythrocyte portion of whole blood;
   the other of said phases is an aqueous liquid external equilibrium phase which is relatively polar and which is capable, when introduced into said circulation, of functioning as a substitute for at least part of the plasma portion of whole blood;
   said relatively non-polar coacervate phase is insoluble in and in equilibrium with said relatively polar external equilibrium phase;
   said two phase liquid system comprises water, a surface active agent, an electrolyte and albumin in amounts effective for the formation of said two phases, and to obtain osmotic pressure and viscosity similar to that of whole blood;
   whereby said two phase liquid system, upon introduction into said circulation, can establish, reestablish and maintain normal osmotic pressures, and can transport and transfer oxygen, carbon dioxide and other physiological gases, and carry nutrients, drugs and various physiological entities in stable form over extended periods of time.

2. A synthetic whole blood substitute according to claim 1, wherein the phases are emulsified with said relatively non-polar coacervate phase in the form of coacervate droplets suspended in said relatively polar liquid aqueous phase.

3. A synthetic whole blood substitute according to claim 1, wherein the pH of the two phase liquid system is in the range of from about 7.3 to 7.45.

4. A synthetic while blood substitute, consisting essentially of a non-toxic two phase liquid system, both said phases being aqueous, wherein:
   one of said phases is an aqueous liquid coacervate phase (internal suspension phase) which is relatively non-polar and which is capable, when introduced into a body's circulation, of functioning as a substitute for at least part of the erythrocyte portion of whole blood;
   the other of said phases is an aqueous liquid external equilibrium phase which is relatively polar and which is capable, when introduced into said circulation, of functioning as a substitute for at least part of the plasma portion of whole blood;
   said relatively non-polar coacervate phase is soluble in and in equilibrium with said relatively polar external equilibrium phase;
   said two phase liquid system comprises albumin, a phospholipid and sodium chloride in amounts effective for the formation of said two phases, and to obtain osmotic pressure and viscosity similar to that of whole blood;
   whereby said two phase liquid system, upon introduction into said circulation, can establish, reestablish and maintain normal osmotic pressures, and can transport and transfer oxygen, carbon dioxide and other physiological gases, and carry nutrients, drugs and various physiological entities in stable form over extended periods of time.

5. A synthetic whole blood substitute according to claim 4, wherein the phospholipid is selected from group consisting of lecithin, cephalin, isolecithin, sphingomyelin, phosphatidyl serine, phosphatidic acid, phosphatidyl inositol, phosphatidyl choline and mixtures thereof.

6. A synthetic whole blood substitute according to claim 5, wherein the phospholipid is lecithin.

7. A synthetic whole blood substitute according to claim 4, wherein at least one of the aqueous phases further includes urea, stroma free hemoglobin, or sterols, or mixtures thereof.

8. A synthetic whole blood substitute according to claim 4 or 7, wherein at least one of the aqueous phases further includes enzymes, metabolic agents, therapeutic drugs or nutrients, or mixtures thereof.

9. A synthetic whole blood substitute according to claim 7, wherein the sterol is selected from cholesterol, ergosterol, 7-dehydrocholesterol, $\alpha$ sitosterol, $\beta$ sitosterol, $\gamma$ sitosterol or campesterol and mixtures thereof.

10. A synthetic whole blood substitute according to claim 4, wherein the electrolytes include KCl or $CaCl_2$ or mixtures thereof.

11. A process for preparing a synthetic whole blood substitute, consisting essentially of a non-toxic two phase liquid system, both said phases being aqueous, comprising the steps of: dispersion albumin in an aqueous solution which includes sodium chloride adding to said solution a phospholipid and an electrolyte; thoroughly mixing said solution; storing said mixture undisturbed for a period of time to form a two phase coacervate system;
   one of said phases being an aqueous liquid coacervate phase (internal suspension phase) which is relatively non-polar and which is capable, when introduced into a body's circulation, of functioning as a substitute for at least part of the erythrocyte portion of whole blood;
   the other of said phases being an aqueous liquid external equilibrium phase which is relatively polar and which is capable, when introduced into said circulation, of functioning as a substitute for at least part of the plasma portion of whole blood;
   said relatively non-polar coacervate phase being insoluble in and in equilibrium with said relatively polar external equilibrium phase;
   whereby said two phase liquid system, upon introduction into said circulation, can establish, reestablish and maintain normal osmotic pressures, and can transport and transfer oxygen, carbon dioxide and other physiological gases, and carry nutrients, drugs and various physiological entities in stable form over extended periods of time.

12. A process according to claim 11, including the step of adding to said two phase coacervate system such amounts of sodium chloride and water to render the system isotonic with whole human blood.

13. A process according to claim 11, including the step of emulsifying said two phase liquid system so that said relatively non-polar coacervate phase is in the form of droplets suspended in said relatively polar liquid aqueous phase.

14. A process according to claim 11, wherein the phospholipid is selected from the group consisting of lecithin, cephalin, isolecithin, sphingomyelin, phosphatidyl serine, phosphatidic acid, phosphatidyl inositol, phosphatidyl choline and mixtures thereof.

15. A process according to claim 14, wherein the phospholipid is lecithin.

16. A process according to claim 11, including the step of admixing urea, stroma free hemoglobin, sterols, or mixtures thereof, in at least one of said aqueous phases.

17. A process according to claim 11, including the step of admixing enzymes, metabolic agents, therapeutic drugs, nutrients or mixtures thereof, in at least one of said aqueous phases.

18. A process according to claim 16, wherein the sterol is selected from the group consisting of cholesterol, ergosterol, 7-dehydrocholesterol, $\alpha$ sitosterol, $\beta$ sitosterol, $\gamma$ sitosterol and campesterol and mixtures thereof.

19. A process according to claim 11, wherein the electrolytes are selected from the group consisting of KCl, $CaCl_2$, and mixtures thereof.

* * * * *